United States Patent [19]
Uematsu

[11] Patent Number: 5,958,227
[45] Date of Patent: Sep. 28, 1999

[54] LIQUID CHROMATOGRAPH APPARATUS WITH A SWITCHING VALVE

[75] Inventor: Gen-ichi Uematsu, Sagamihara, Japan

[73] Assignee: Tosoh Corporation, Japan

[21] Appl. No.: 09/114,497

[22] Filed: Jul. 13, 1998

[51] Int. Cl.[6] .................................................. B01D 15/08
[52] U.S. Cl. ...................................... 210/198.2; 210/659
[58] Field of Search ................................... 210/635, 656, 210/659, 143, 198.2

[56] References Cited

U.S. PATENT DOCUMENTS

| | | | |
|---|---|---|---|
| 4,017,262 | 4/1977 | Small | 210/284 |
| 4,452,067 | 6/1984 | Ahlstrom, Jr. et al. | 73/23.1 |
| 4,567,753 | 2/1986 | Miller, Jr. et al. | 73/61.1 C |
| 4,577,492 | 3/1986 | Holba et al. | 73/61.1 C |
| 5,071,547 | 12/1991 | Cazer | 210/198.2 |
| 5,547,497 | 8/1996 | Klemp | 96/104 |
| 5,567,307 | 10/1996 | Karmarkar | 210/198.2 |
| 5,652,398 | 7/1997 | Johnson | 73/863.71 |

FOREIGN PATENT DOCUMENTS

| | | | |
|---|---|---|---|
| 0 230 307 | 7/1987 | European Pat. Off. | 210/198.2 |
| 0 359 322 | 3/1990 | European Pat. Off. | 210/198.2 |

*Primary Examiner*—Ernest G. Therkorn
*Attorney, Agent, or Firm*—Nixon & Vanderhye

[57] ABSTRACT

A liquid chromatograph apparatus has a precolumn and an analyzing column which are connected through a 8-port-two-position-switching valve wherein the switching valve is capable of switching between two movable positions wherein a flow path for a solvent directing from the precolumn to the analyzing column is formed in one of the two movable positions; a flow path for the solvent directing from the analyzing column to the precolumn is formed in the other of the two movable positions, and the flow paths formed in the two movable positions are such that flowing directions of the solvent in the precolumn are opposite and flowing directions of the solvent in the analyzing column are the same.

5 Claims, 12 Drawing Sheets

ANALYZING STEP, FLOW PATH 1

CLEANING STEP, FLOW PATH 2

FIGURE 1

ANALYZING STEP, FLOW PATH 1

CLEANING STEP, FLOW PATH 2

FIGURE 2

ANALYZING STEP, FLOW PATH 1

CLEANING STEP, FLOW PATH 2

FIGURE 3

ANALYZING STEP, FLOW PATH 1

CLEANING STEP, FLOW PATH 2

ANALYZING STEP, FLOW PATH 1

CLEANING STEP, FLOW PATH 2

STEPS OF SUCKING, CLEANING / HEATING AND SUCKING SAMPLE

STEP OF INTRODUCTION

FIGURE 12

FIGURE 13a — CLEANING LIQUID SUCKING STEP

FIGURE 13b — CLEANING/HEATING STEP

FIGURE 13c — SAMPLE SUCKING STEP

FIGURE 13d — INJECTING STEP

SAMPLING OPERATIONS

TO ANALYZING COLUMN

FROM PUMP

FIGURE 16

LIQUID CHROMATOGRAPH APPARATUS WITH A SWITCHING VALVE

The present invention relates to a liquid chromatograph apparatus with a switching valve. In particular, it relates to a liquid chromatograph apparatus in which a flowing direction of solvent in a first column is reversed with the switching valve. More particularly, it relates to a liquid chromatograph apparatus provided with a sample injecting means which is preferably used for high temperature liquid chromatography capable of analyzing under an elevated temperature condition.

Figure 9:
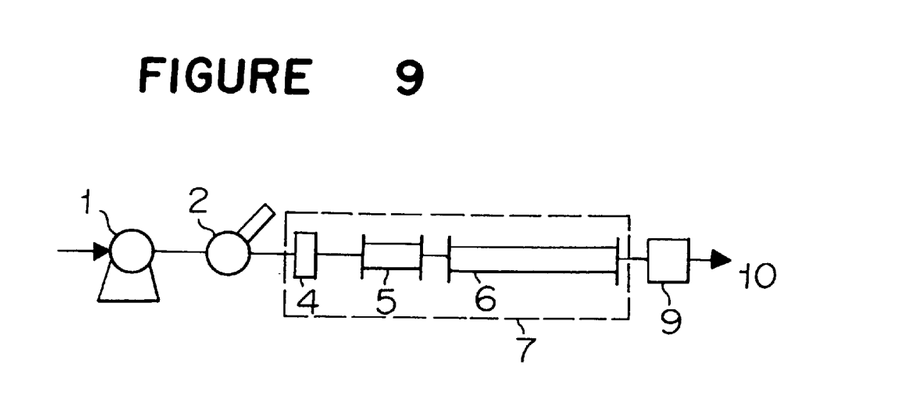
FIG. 9 is a diagram showing a structure of a flow path in the typical liquid chromatograph apparatus.

When analysis is conducted by liquid chromatography such as high performance chromatography (hereinbelow, referred to simply as HPLC), scraps resulted due to wearing of sealing materials for the pump and the valve and impurities contained in a solvent and/or a sample are deposited on an end of a column. Since the scraps and the impurities deposited cause a reduction in the performance of an analyzing column, a technique of inserting a precolumn between a sample injecting portion and the analyzing column has frequently been utilized, as shown in FIG. 9, so that the analyzing column is protected from deterioration. In such technique, the precolumn, after having been used for a predetermined time, is disposed to be replaced by a new one, or it is removed from the liquid flowing system so that it is subjected to a cleaning/regeneration treatment (hereinbelow, referred to simply as regeneration), and then, the regenerated precolumn is returned to the system.

In HPLC in a reversed phase chromatography or ion chromatography, there is a proposed method wherein the precolumn is connected to the analyzing column by means of a switching valve so that the precolumn can be regenerated. In this method, two kinds of solvent, i.e., a solvent for analyzing and a solvent for regeneration, and a plurality of pumps for feeding the solvents are required. When analysis is conducted, a flow path for feeding the solvent for analyzing in the order of the precolumn and the analyzing column is formed. When the precolumn is to be regenerated, the solvent for regeneration is fed only in the precolumn followed by discharging it out of the liquid flowing system, and on the other hand, a flow path for feeding the solvent for analyzing in the analyzing column is formed.

Figure 16:
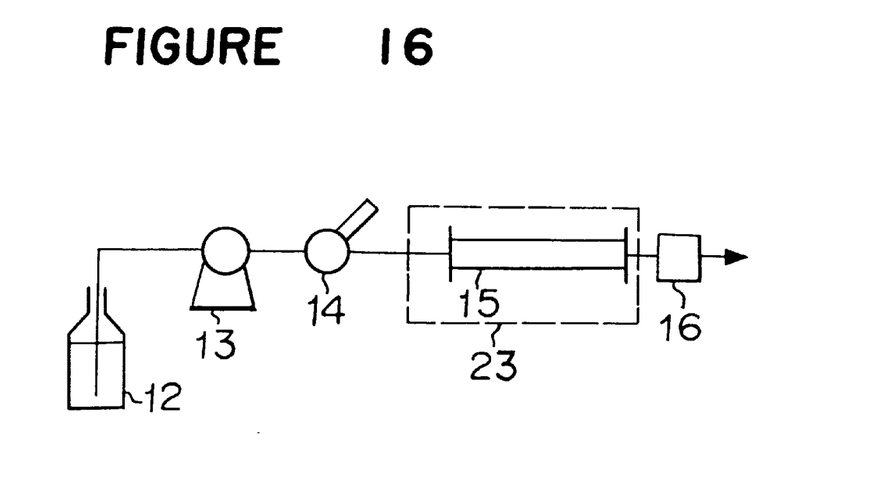
FIG. 16 is a diagram showing a general structure of HPLC.

FIG. 16 is a diagram showing a typical example of a mechanical structure for HPLC wherein reference numeral 12 designates a solvent, 13 a liquid supply pump, 14 a sample injecting apparatus, 15 an analyzing column, 23 a column oven and 16 a detector. A sample is injected through the sample injecting apparatus along with a flow of solvent to be introduced into a flow path for HPLC. Then, the sample is separated in the analyzing column 15 and is fed into the detector in which the concentration of the sample is measured.

In HPLC, a correct result of analysis can not be obtained unless the sample is completely dissolved in the solvent used as a mobile phase. In particular, when a sample to be analyzed by gel permeation chromatography for analyzing a distribution of the molecular weight (hereinbelow, referred to as GPC) is a synthesized polymer, there is an essential problem as to how the sample can be dissolved in the solvent.

A generally used polymer can be dissolved in a solvent at about 60° C. Accordingly, it is relatively easy to conduct analysis on a distribution of the molecular weight. However, it is difficult to dissolve polyolefin such as polyethylene or polypropylene in the solvent at about 60°0 C. A conventional technique proposes to add a high-boiling solvent such as o-dichlorobenzene (ODCB) or trichlorobenzene (TCB) and to heat it to about 150° C. to dissolve whereby the analysis of a distribution of the molecular weight is conducted by GPC.

In the conventional technique, in order to conduct analysis under a high temperature condition such as 150° C., it is necessary not only to keep a high temperature condition by placing the analyzing column in a column oven or the like, but also to keep the sample under a high temperature condition so as not to cause the precipitation of the sample in a pipe in the sample injecting apparatus when the sample is injected. Further, it is necessary to keep the portion other than the sample injecting apparatus under a high temperature condition so as not to cause the precipitation of the sample after the sample injection.

Figure 15:
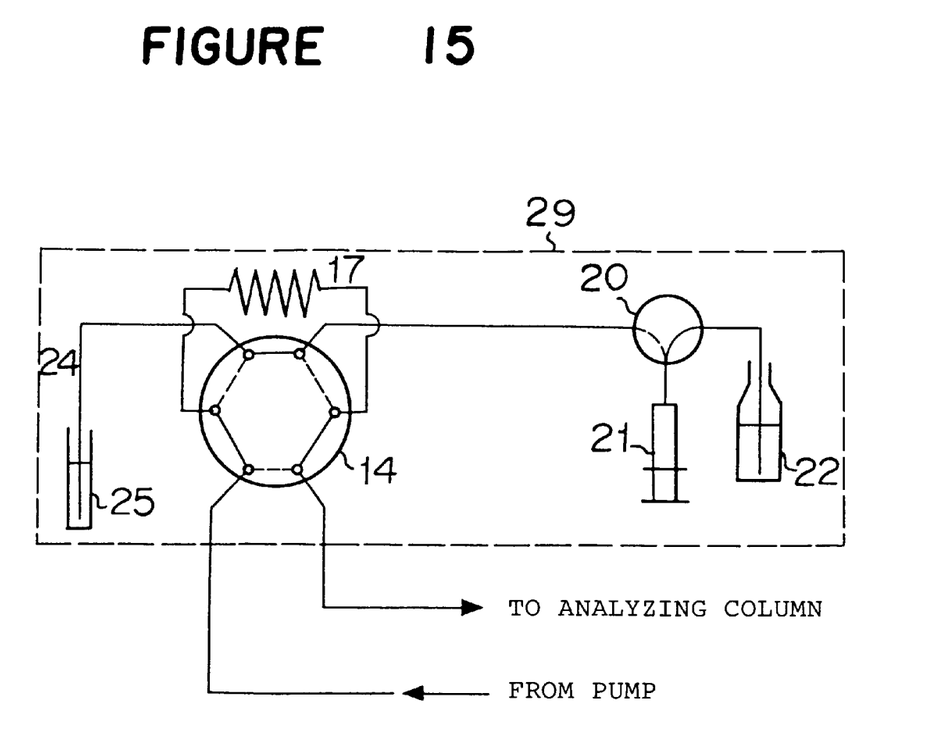
FIG. 15 is a diagram showing a conventional sample injecting apparatus used under a high temperature condition.

In order to meet such requirements, there is proposed a conventional HPLC apparatus as shown in FIG. 15 wherein a sample injecting means (a 6-port-switching valve) 14 including a sample 25, a sampling needle 24 and a sampling loop 17, a syringe 21 as a metering means and a cleaning liquid containing vessel 22 are arranged in an oven 29 so that they are kept in the same elevated temperature condition as the analyzing column.

Since the columns used for HPLC are expensive, the disposal of the precolumn is not preferable from the viewpoint of cost performance. However, when the precolumn is continuously used for a long time, there causes a problem that scraps or impurities are deposited on the precolumn to increase a pressure. Accordingly, after a continuous use of the precolumn, the regeneration is needed. In a technique to remove the precolumn from the liquid flowing system to regenerate it, it is necessary to feed a solvent to the removed precolumn in the direction opposite to the direction of feeding the solvent during the analysis whereby scraps deposited at an inlet side of the precolumn are washed off. In this case, there is a problem that it takes a longer time to remove the precolumn from the liquid flowing system, and therefore, an analyzing operation has to be interrupted.

In the technique, as proposed for the reversed phase chromatography or ion chromatography, that the precolumn is connected to the analyzing column through a switching valve wherein regeneration can be effected by feeding a solvent for regeneration, it is unnecessary to remove the precolumn from the liquid flowing system and a time required for interruption of the analysis can be short. However, there is a problem that the above-mentioned regeneration can not be employed because the GPC requires use of only a single kind of solvent for analyzing. Accordingly, when the method as proposed for the reversed phase separation mode or the ion chromatography is employed in the GPC, a liquid supply means such as a pump is additionally required and a solvent for regeneration is additionally required.

Further, in the GPC, analysis is mainly conducted by using a refractive index detector. Since the refractive index detector requires a longer time for stabilization and is sensitive to a change in the solvent and a change of temperature. Accordingly, the additional use of the solvent for regeneration to carry out the regeneration of the precolumn results an additional problem of requiring operation for equilibrating the precolumn and the liquid flowing system by using the solvent for analyzing. Such equilibrating operation is also needed when the precolumn is to be replaced. As a result, there is still a problem that it takes a much time for stabilizing the detector in replacing or regenerating the precolumn when the method of regeneration as proposed for the reversed phase separation mode or the ion chromatography is conducted.

Further, in the conventional liquid chromatograph apparatus used for high-temperature HPLC, in particular, for GPC analysis at a high temperature, the apparatus comprises the sample injecting means 14 provided with the sampling needle and the sampling loop 17, the metering means 21 such as a syringe, the cleaning liquid containing vessel 22 and the oven 29 and so on as shown in FIG. 15. In the conventional apparatus, the sampling needle and mechanically movable parts such as the syringe as a metering means for sucking a predetermined amount of liquid are kept under a temperature condition so as to assure reliable operations. Since movable mechanical parts perform a vertical movement, a lateral movement and a rotational movement, durability is apt to decrease under a high temperature condition with the result that a trouble such as a defective movement may occur.

Further, of elements constituting the sample injecting apparatus, portions such as a sealing material which are in contact with liquid components such as the sample, the solvent, the cleaning liquid and so on are mainly composed of a fluoride resin such as polytetrafluoroethylene or the like from the viewpoints of solvent resistance and pressure resistance. However, the fluoride resin shows a remarkable reduction of strength under a high temperature condition such as 100° C. or more whereby liquid leakage may take place.

The cleaning liquid is heated to a high temperature so that the sampling needle stained with the sample liquid is washed while preventing the precipitation of the sample. Accordingly, a cleaning liquid containing vessel is placed in an oven to keep the cleaning liquid in the vessel under a high temperature condition in the same manner as the analyzing column. Under such high temperature condition, however, the cleaning liquid may evaporate to leak out of the apparatus.

Accordingly, it is an object of the present invention to provide a liquid chromatograph apparatus for HPLC which minimizes as possible opportunities of exchanging of the precolumn and do not require the equilibration of the precolumn and other elements after the regeneration of the precolumn even in a GPC, by simplifying the regeneration of the precolumn with use of a solvent for analyzing while there is no need for additional elements.

It is another object of the present invention to provide a sample injecting apparatus which minimizes occurrence of a defective operation of the mechanical elements; prevents a reduction of strength of sealing materials used for the mechanical elements; and prevents evaporation of the cleaning liquid and the leakage out of the apparatus, by keeping a necessary minimum number of mechanical elements under a high temperature condition.

In accordance with a first aspect of the present invention, there is provided a liquid chromatograph apparatus comprising a first column and a second column which are connected through a switching means, the liquid chromatograph apparatus being characterized in that the switching means comprises a valve body capable of switching between two movable positions wherein a flow path for a solvent directing from the first column to the second column is formed in one of the two movable positions; a flow path for the solvent directing from the second column to the first column is formed in the other of the two movable positions, and the flow paths formed in the two movable positions are such that flowing directions of the solvent in the first column are opposite and flowing directions of the solvent in the second column are the same.

In a second aspect of the present invention, there is provided the liquid chromatograph apparatus according to the first aspect wherein the switching means is a two-position-switching valve having at least 8 ports. In a third aspect of the present invention, there is provided the liquid chromatograph apparatus according to the first aspect wherein the switching means is formed by combining two or more two-position-switching valves each having at least 6 ports.

Although the above-mentioned are useful in particular for HPLC in a GPC, they are also useful in a case that a single solvent is fed to the first column and the second column not only for the regeneration but also for the analysis.

In accordance with a fourth aspect of the present invention, there is provided the liquid chromatograph apparatus according to the first aspect, which further comprises a sample injecting apparatus including a sample injecting means provided with a sampling needle and a sampling loop, a first heat exchanger, a second heat exchanger, a metering means and a cleaning liquid containing vessel, wherein a portion of the sample injecting means excluding at least the sampling needle and the first heat exchanger are kept under the same temperature condition as the columns; at least the second heat exchanger, the metering means and the cleaning liquid containing vessel are kept at a temperature different from the temperature in that portion and the first heat exchanger; and the sample injecting means, the first heat exchanger, the second heat exchanger, the metering means and the cleaning liquid containing vessel are connected in series.

In a fifth aspect of the present invention, there is provided the liquid chromatograph apparatus according to the fourth aspect, wherein the sample injecting means is a two-position-switching valve having 6 ports.

DESCRIPTION OF THE PREFERRED EMBODIMENTS

Preferred embodiments of the present invention will be described with reference to the drawings.

Figure 1:
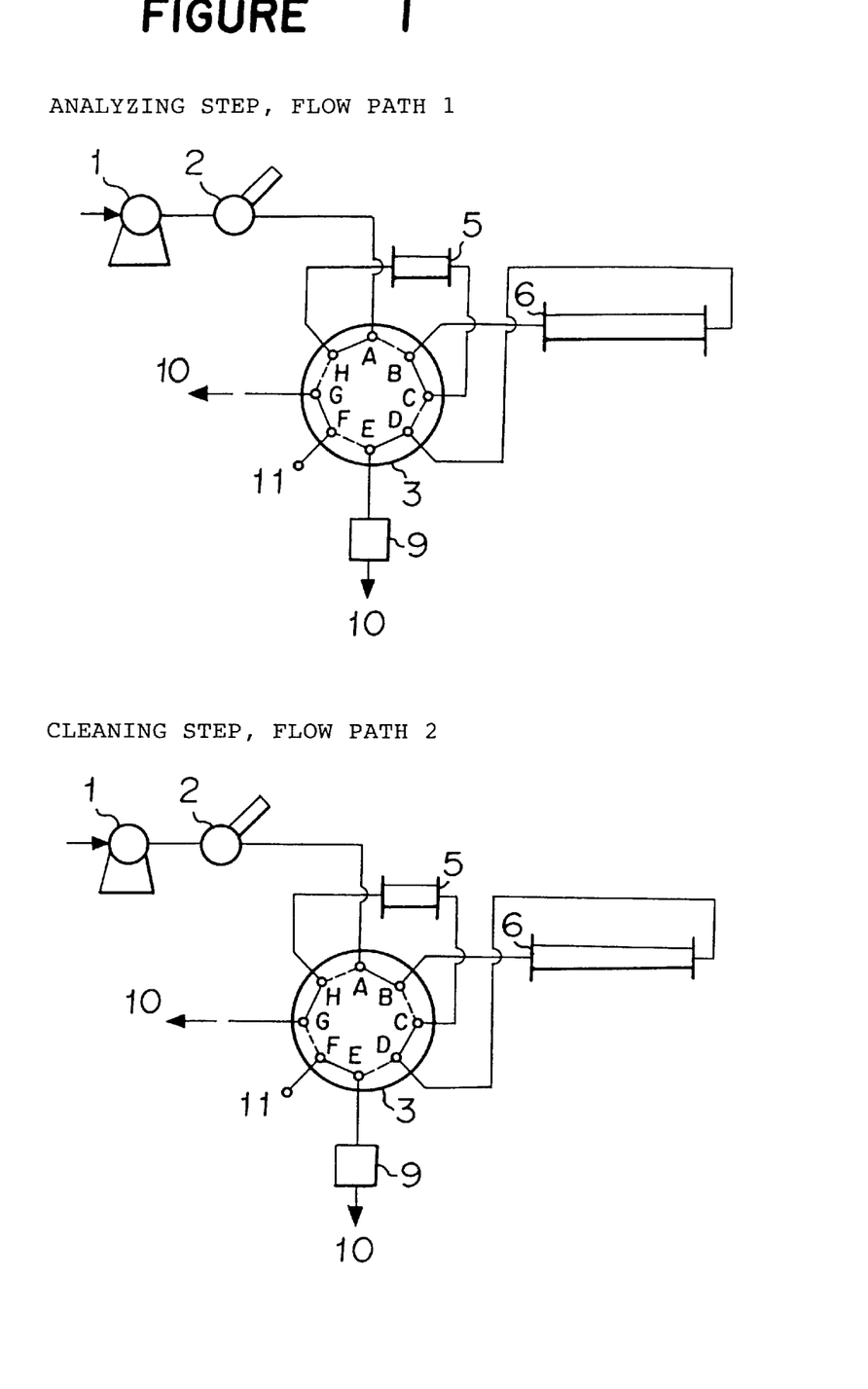
FIG. 1 is a diagram showing an embodiment of the liquid chromatograph apparatus according to the present invention.
Figure 7:
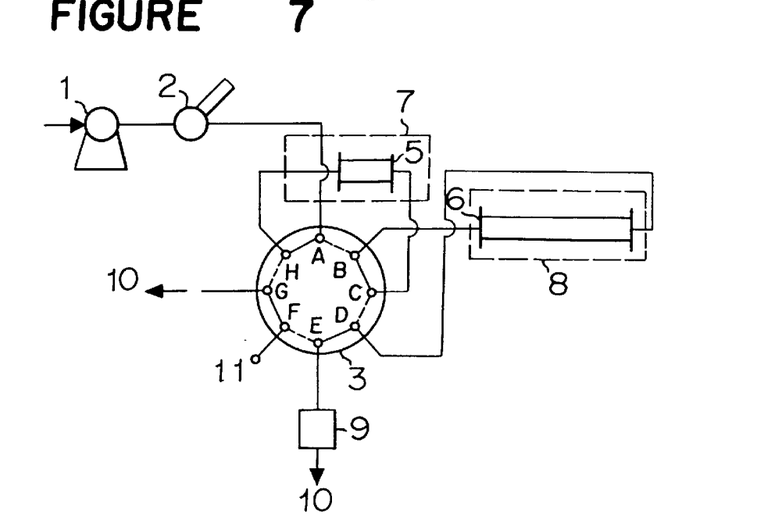
FIG. 7 is a diagram showing the liquid chromatograph apparatus in a GPC used in an example of the present invention.

FIG. 1 shows schematically the liquid chromatograph apparatus according to the second aspect of the present invention, which is provided with a two-position-switching valve having 8 ports (hereinbelow, referred to as a 8-port-2-position-switching valve) as the switching means. In FIG. 1, reference numeral 1 designates a pump, numeral 2 a sample injecting apparatus, numeral 3 a 8-port-2-position-switching valve, numeral 4 a filter, numeral 5 a precolumn (a first column), numeral 6 an analyzing column (a second column), numeral 9 a detector and numeral 10 an outlet of waste solution. The precolumn and the analyzing column may respectively be housed in an oven 7 for precolumn and an oven 8 for analyzing column as shown in FIG. 7. An upper portion of FIG. 1 shows a flow path formed when analysis is conducted and a lower portion of FIG. 1 shows a flow path formed when the precolumn is regenerated.

In the liquid chromatograph apparatus according to the fourth aspect of the present invention, the sample injecting apparatus shown in FIG. 2 may have such structure described below.

When analysis is to be conducted, there is formed a flow path: a port A of switching valve-a port H-the precolumn 5-a port C-a port B-the analyzing column 6-a port D-a port E-the detector 9, whereby the solvent is supplied successively through the precolumn (at a side A)-the precolumn (at a side B)-the analyzing column 6-the detector 9 in this order, during which impurities of the solvent and the sample and/or scraps of the sealing material for the pump and so on are deposited at an end (at a side A) of the precolumn 5.

When the precolumn 5 is to be regenerated, a switching operation is performed for the switching valve whereby there is formed a flow path: a port A of switching valve-a port B-the analyzing column 5-a port D-a port C-the precolumn 5-a port H-a port G. Accordingly, the solvent is supplied successively through the analyzing column 6-the precolumn (at a side B)-the precolumn (at a side A) to be discharged. During the supply of the solvent, the impurities of the solvent and the sample deposited at the end of the precolumn 5 (at a side A) and/or the scraps of the sealing material of the pump and so on are washed off by the solvent discharged out of the system. In this case, the washed-off impurities and so on are discharged out of the system without passing through the analyzing column 6, and accordingly, there is no danger of damaging the analyzing column.

Figure 2:
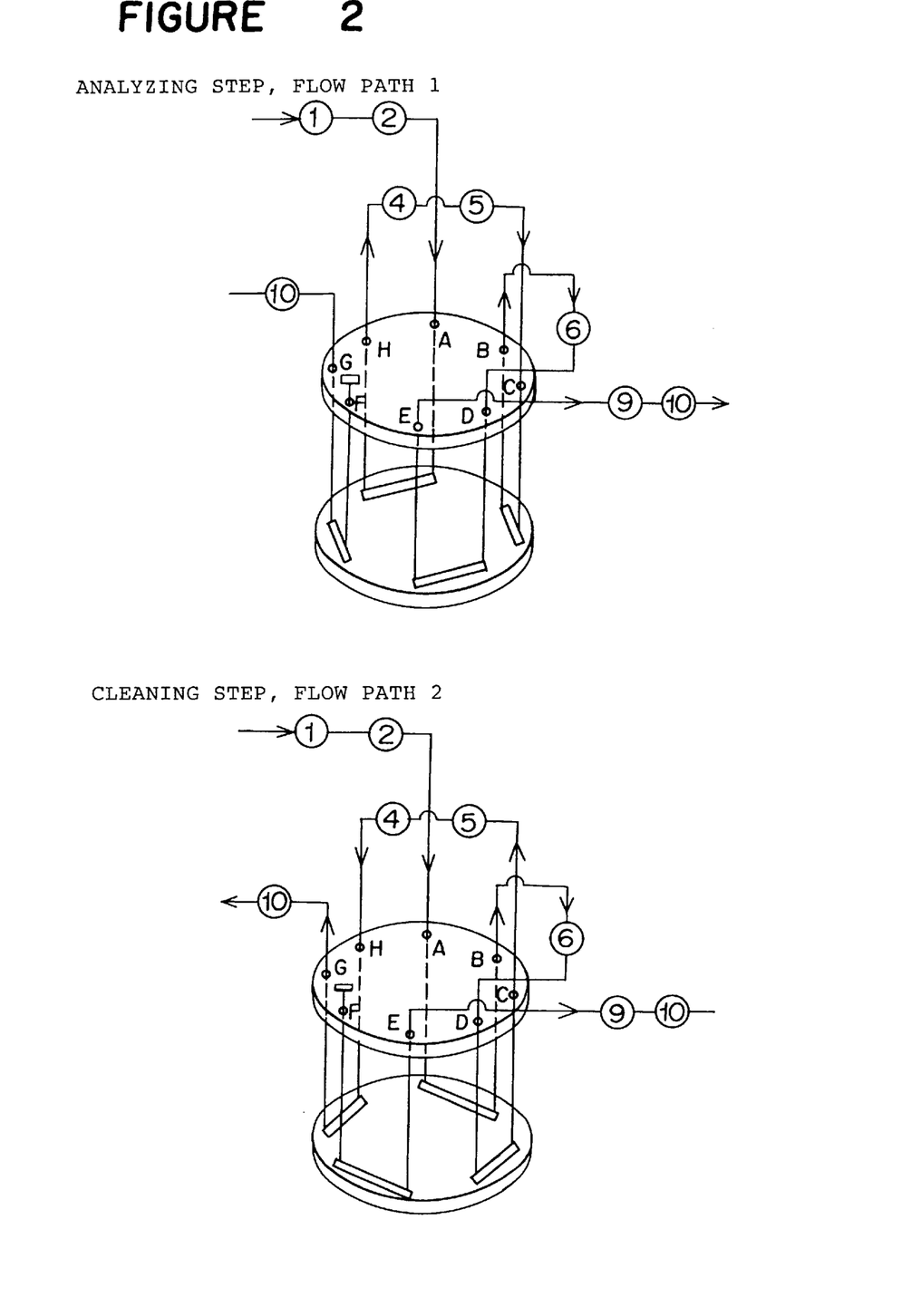
FIG. 2 is a diagram showing in detail a 8-port-switching valve.

FIG. 2 shows in more detail the 8-port-2-position-switching valve shown in FIG. 1. The switching valve is mainly constituted by a fixed face referred to as a stator and a working face referred to as a rotor. The rotor has through holes formed at equal angular intervals of 45°. On the other hand, the stator has grooves which are alternately formed at equal angular intervals of 45°. FIG. 2 shows the stator and the rotor in a separated state in order to clarify the structure of the switching valve. In fact, however, the both members are in close contact with each other and flowing paths are formed by rotating the rotor by 45°.

Figure 3:
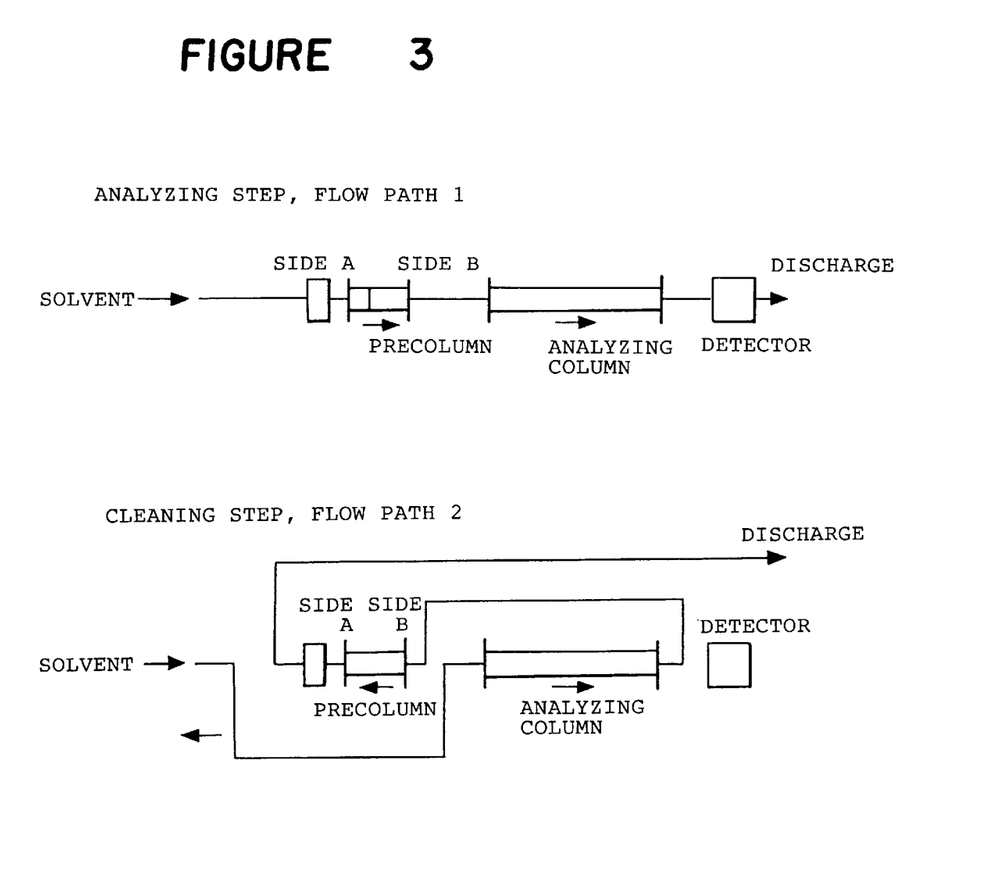
FIG. 3 is a diagram for explaining flowing directions of solvent in a first column and a second column.

FIG. 3 is a diagram showing directions of solvent flowing in the precolumn (the first column). As described above, in analyzing a sample (an upper portion of FIG. 3), the solvent flows in a direction of analyzing column 6. On the other hand, in regenerating the precolumn (a lower portion of FIG. 3), the solvent flows in the direction opposite to the case of analyzing. With respect to the analyzing column (the second column), the solvent is always passed in a constant direction irrespective of analyzing or regenerating. Namely, although two ways of solvent flow path are formed depending on movable positions by operating the switching valve, the flowing directions of the solvent are opposite to each other in the first column while the flowing directions of the solvent are the same in the second column.

Figure 4:
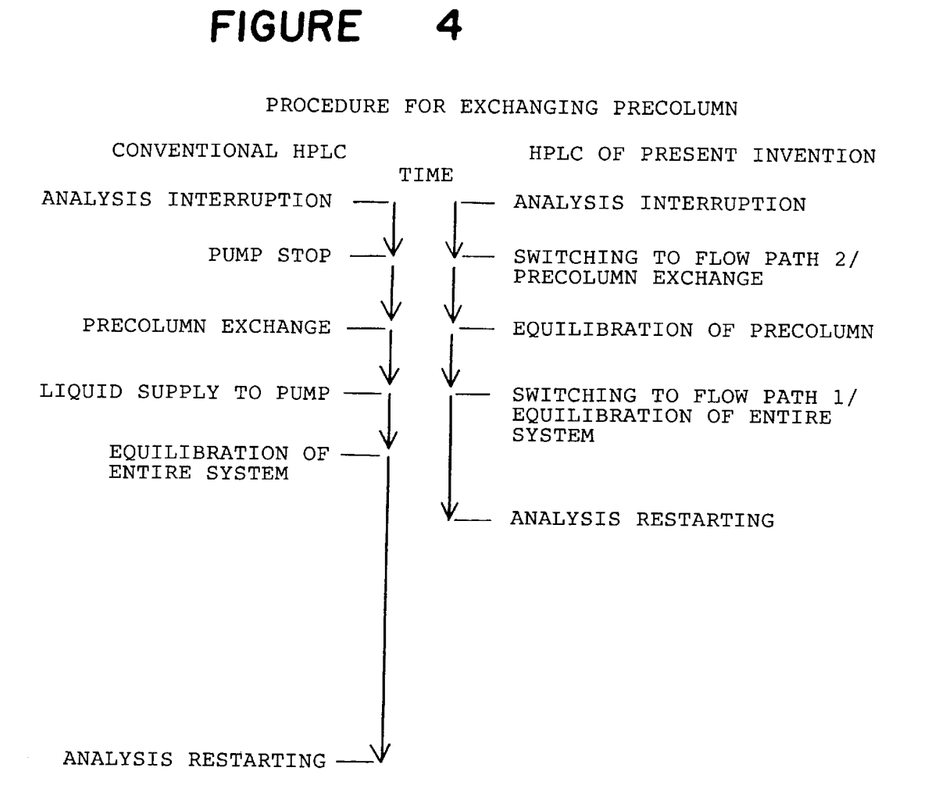
FIG. 4 is a diagram for explaining a process for exchanging a precolumn.

FIG. 4 is a diagram for explaining a case that the precolumn is exchanged. In cases of the first to third aspects of the present invention, the precolumn can easily be regenerated to thereby minimize the necessity of exchange. However, these are also effective even in a case of exchanging the precolumn. In the ordinary HPLC, the exchange of the precolumn should be conducted by stopping the liquid supplying operation of the pump (as shown in a left side in FIG. 4). The stop of the liquid supply is essential because the precolumn is connected in series to the analyzing column. After the precolumn has been exchanged, it is necessary to conduct equilibration of the interior of the columns and the detector by restarting liquid supply by the pump. A new precolumn is filled with a solvent (a preserving solvent) other than the solvent used for analyzing. After the exchange, it is gradually substituted with the solvent used for analyzing. Since the preserving solvent flows successively through the precolumn, the analyzing column and the detector, the equilibrium of the analyzing column which was in a stable state is once lost. Further, since a temperature of the new column is different from that of the analyzing column, equilibrium of temperature is also lost. Thus, after the precolumn has been exchanged, it takes a much time to obtain a state of equilibrium.

In the first to third aspects of the present invention, the exchange of the precolumn and the equilibrating operation of the precolumn can be performed in a shorter time by switching the valve (as shown in a right side of FIG. 4). In the exchange of the precolumn, the flow path used for regenerating the precolumn is used. When the precolumn is exchanged in this state and solvent substitution is conducted for the precolumn, the preserving solvent in the new precolumn is discharged directly out of the system without being introduced into the analyzing column. Then, the switching operation is conducted to form the flow path usable for analyzing whereby an analyzing operation can be restarted in a shorter time. In this case, it is unnecessary to stop the liquid supply by the pump during the exchange of the precolumn.

Figure 5:
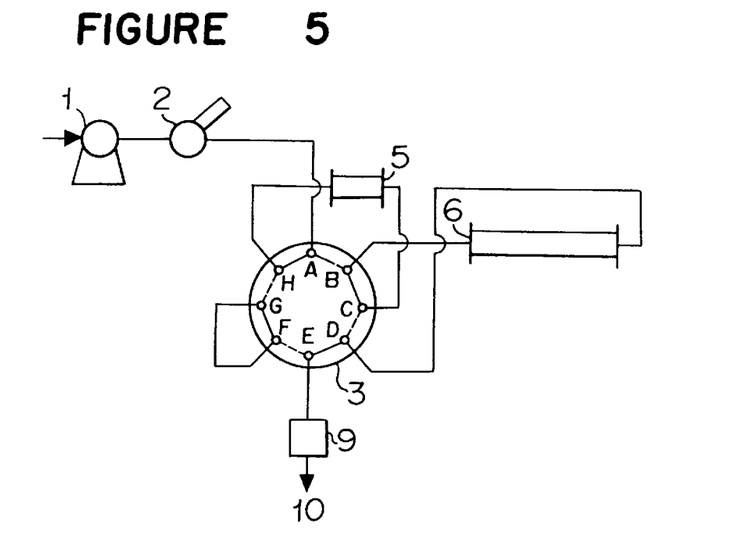
FIG. 5 is a diagram showing an embodiment of the liquid chromatograph apparatus according to the present invention.

In the foregoing, the liquid chromatograph apparatus with the 8-port-2-position-switching valve according to the second aspect of the present invention has been described. However, the liquid chromatograph apparatus may be provided with a switching valve having more than 8 ports. In this case, needless ports may be plugged or a bypass may be formed so that substantially the same flow path as the above-mentioned embodiment can be formed. Further, in the same 8-port-2-position-switching valve, the same flow paths can be formed by bypassing the flow path between ports F and G as shown in FIG. 5. In this case, an outlet of waste solution used for analyzing and an outlet of waste solution used for regeneration are commonly used.

Figure 6:
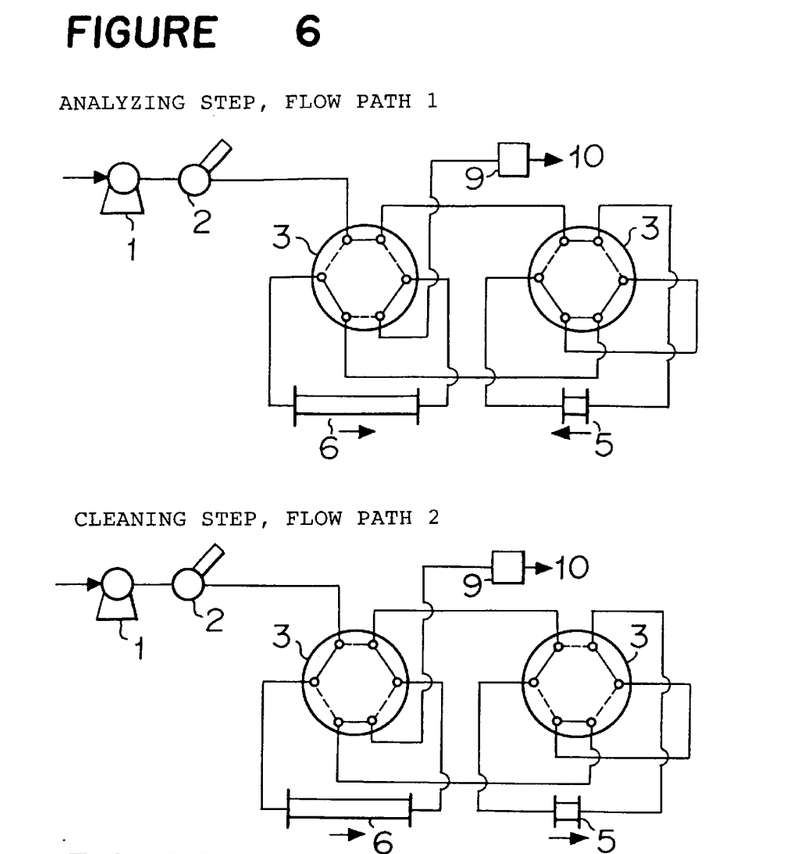
FIG. 6 is a diagram showing another embodiment of the liquid chromatograph apparatus according to the present invention.

In the third aspect of the present invention, the same flow paths as described above can be formed by combining a plurality of switching valves having at least 6 ports. FIG. 6 shows an embodiment of the liquid chromatograph apparatus according to the third aspect of the present invention wherein two switching valves having 6 ports are used in combination.

Further, in the first to third aspects of the present invention, the first column and/or the second column may be a group of columns connected in series.

The liquid chromatograph apparatus according to the fourth and fifth aspects of the present invention comprises, in addition to the elements as described in the first aspect, a sample injecting apparatus including a sample injecting means provided with a sampling needle and a sampling loop, a first heat exchanger, a second heat exchanger, a metering means and a cleaning liquid containing vessel, wherein a portion of the sample injecting means excluding at least the sampling needle and the first heat exchanger are kept under the same temperature condition as the columns; at least the second heat exchanger, the metering means and the cleaning liquid containing vessel are kept at a temperature different from the temperature in that portion and the first heat exchanger; and the sample injecting means, the first heat exchanger, the second heat exchanger, the metering means and the cleaning liquid containing vessel are connected in series.

The sample injecting apparatus is suitable for conducting high temperature HPLC by which a sample is analyzed under a high temperature condition, and the sample injecting apparatus itself can provide a sufficient effect without being added to the liquid chromatograph apparatus. However, when the sample injecting apparatus is used in combination of the liquid chromatograph apparatus, a preferably high temperature HPLC apparatus can be provided.

Figure 10:
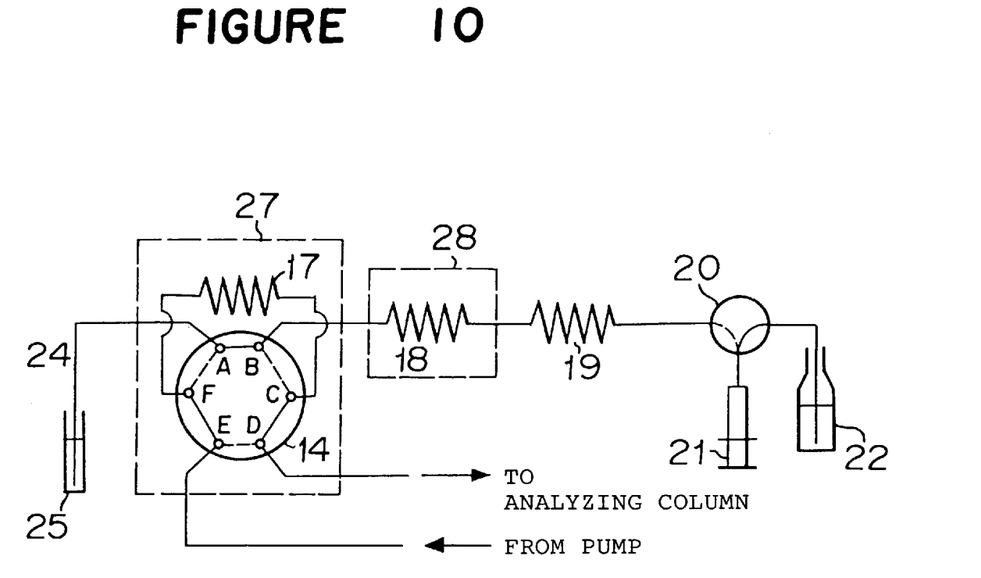
FIG. 10 is a diagram showing an embodiment of the sample injecting apparatus according to the present invention.

FIG. 10 shows an embodiment of the sample injecting apparatus incorporated in the liquid chromatograph apparatus according to the fifth aspect of the present invention. In FIG. 10, reference numeral 24 designates a sampling needle, numeral 14 a sample injecting means (a 6-port-switching valve), numeral 17 a sampling loop, numerals 27 and 28 designate ovens which keep the sample injecting means 14 including the sampling loop 17 and a preheating loop (the first heat exchanger) 18 under the same temperature condition as the analyzing column (not shown), numeral 19 a cooling loop (the second heat exchanger), numeral 20 a switching valve, numeral 21 a metering means (syringe) and numeral 22 a cleaning liquid including vessel. The sampling needle 24 is driven in XYZ directions by a needle driving means (not shown) to be immersed in a sample 25. In the above-mentioned embodiment, a cleaning liquid in the vessel 22 may be the same solvent as the solvent supplied from the liquid supply pump (not shown).

The above-mentioned analyzing apparatus in which the first column and the second column are connected by means of the switching valve, is connected to a port D in the 6-port-switching valve. More specifically, a port A in the 8-port-switching valve in FIG. 1 is connected to the port D in this embodiment. On the other hand, a port E is connected to the liquid supply pump 1 shown in FIG. 1.

The sampling loop 17 in this embodiment is of a spirally wound pipe, the capacity of which is determined depending on an amount of the sample supplied for analyzing. The preheating loop 18 as the first heat exchanger and the cooling loop 19 as the second heat exchanger are both of spirally wound pipes and of a type capable of heat-exchanging when the liquid is passed through these loops. The first heat exchanger 18 is housed in the oven 28 so as to be under a high temperature condition whereby the liquid in the heat exchanger is elevated to a predetermined temperature. The second heat exchanger 19 is, in a case of this embodiment, under a room temperature condition whereby the liquid in the second heat exchanger is brought to the room temperature. The second heat exchanger 19 may be housed in a cooling box other than being placed under the room temperature condition. However, determination as to whether or not the cooling box or the like is used is suitably made in consideration of temperature conditions for the syringe 21 and the cleaning liquid 22.

In the above-mentioned embodiment, the sample injecting means 14 including the sampling loop 17 and the pre heating loop (the first heat exchanger) 18 are respectively housed in the ovens 27, 28 separately. However, they may be disposed in the same oven. The oven or ovens can be one or ones usable for the ordinary HPCL. Temperature in the ovens is controlled to be under the same temperature condition as that in the analyzing means comprising the analyzing column and so on (e.g., the precolumn, the analyzing column, the switching valve and detector in the first to third aspects of the present invention) whereby deposition of the sample can be prevented.

The liquid chromatograph apparatus according to the fourth and fifth aspects of the present invention is suitably usable for high temperature HPLC wherein the sample dissolved under a high temperature condition is analyzed by an analyzing means such as the analyzing column. As an example of analyzing a sample of high temperature in the analyzing column, there is a case that GPC is conducted for the before-mentioned polyolefin or the like (in this case, the sample should be heated to about 150° C.). Even in a case that the sample is heated to about 50° C.–60° C. to be supplied to the analyzing column, the needle in the sample injecting means, the metering means and the cleaning liquid containing vessel can be subjected to a temperature different from the temperature condition for the sample, e.g., under the room temperature condition, whereby problems such as a defective movement of mechanical elements or the evaporation of the cleaning liquid can be prevented. Further, in a case of HPLC wherein a sample of low temperature has to be supplied to the analyzing column, the first heat exchanger can be used as a cooling loop while the second heat exchanger is for a heating loop.

FIG. 10 shows an example of using the 6-port-switching valve as the sample injecting means. However, the present invention is not limited thereto and a 8-port-switching valve can be used, for example. The switching valve 20 in FIG. 10 may be such one as to be used for the ordinary HPLC, e.g. an electromagnetic valve or the like. Further, the syringe pump as a metering means may be substituted with another liquid supply means.

Figure 11:
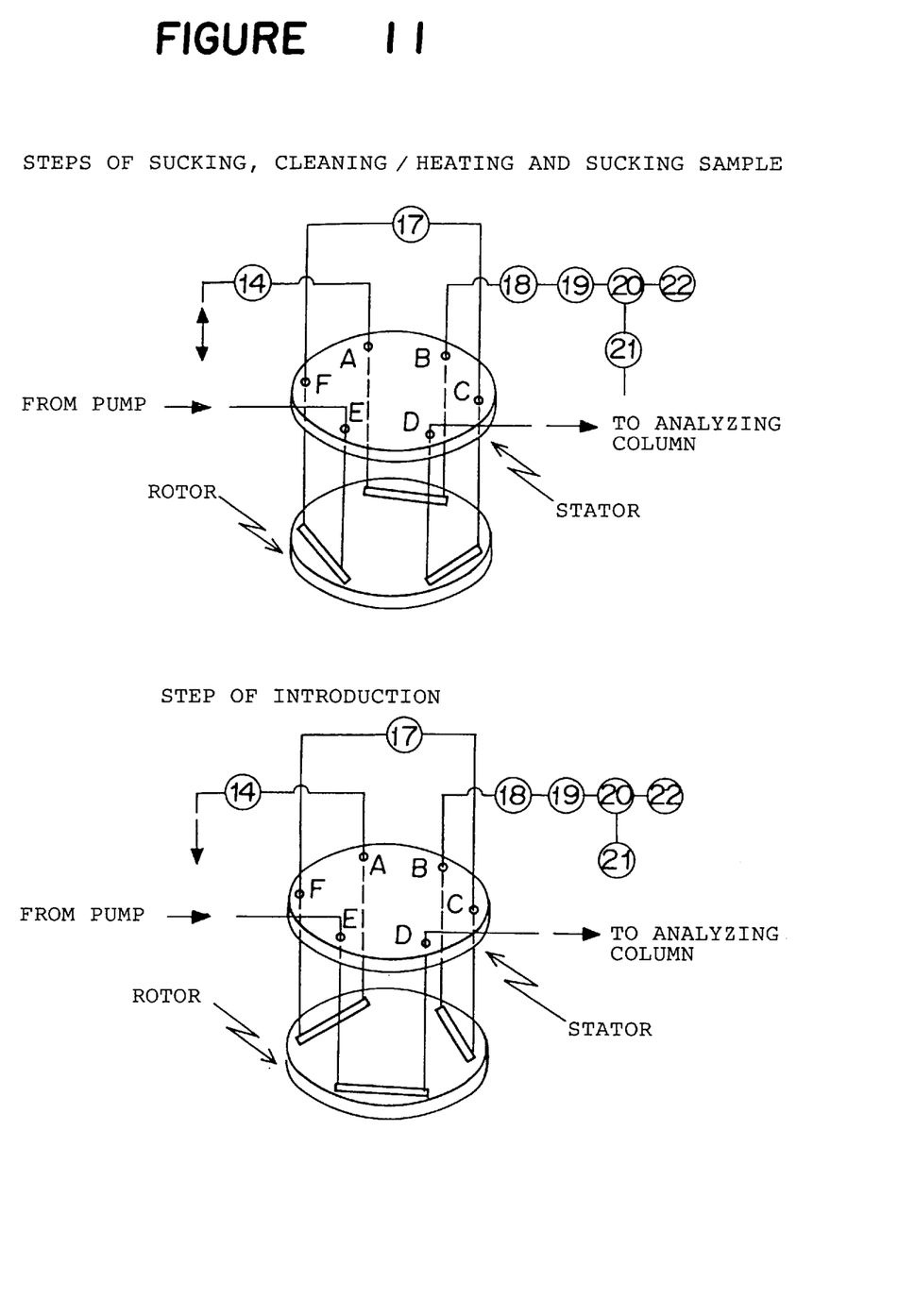
FIG. 11 is a diagram showing in detail a 6-port-switching valve suitable as a sample injecting means in the sample injecting apparatus of the present invention.

FIG. 11 shows in detail the 6-port-switching valve which is suitable as the sample injecting means 14. The 6-port-switching valve is also constituted by a fixed face referred to as a stator and a working face referred to as a rotor in the same manner as the 8-port-switching valve shown in FIG. 2. The stator has through holes formed at angular intervals of 60° and the rotor has three grooves formed at angular intervals of 60° in a triangular form. In the same manner as shown in FIG. 2, the stator and the rotor are in close contact with each other to form flow paths. By turning the rotor by 60°, two kinds of flow path: a flow path 1 and a flow path 2, can be formed. The reference numerals in FIG. 11 are the same as those of FIG. 10.

Figure 12:
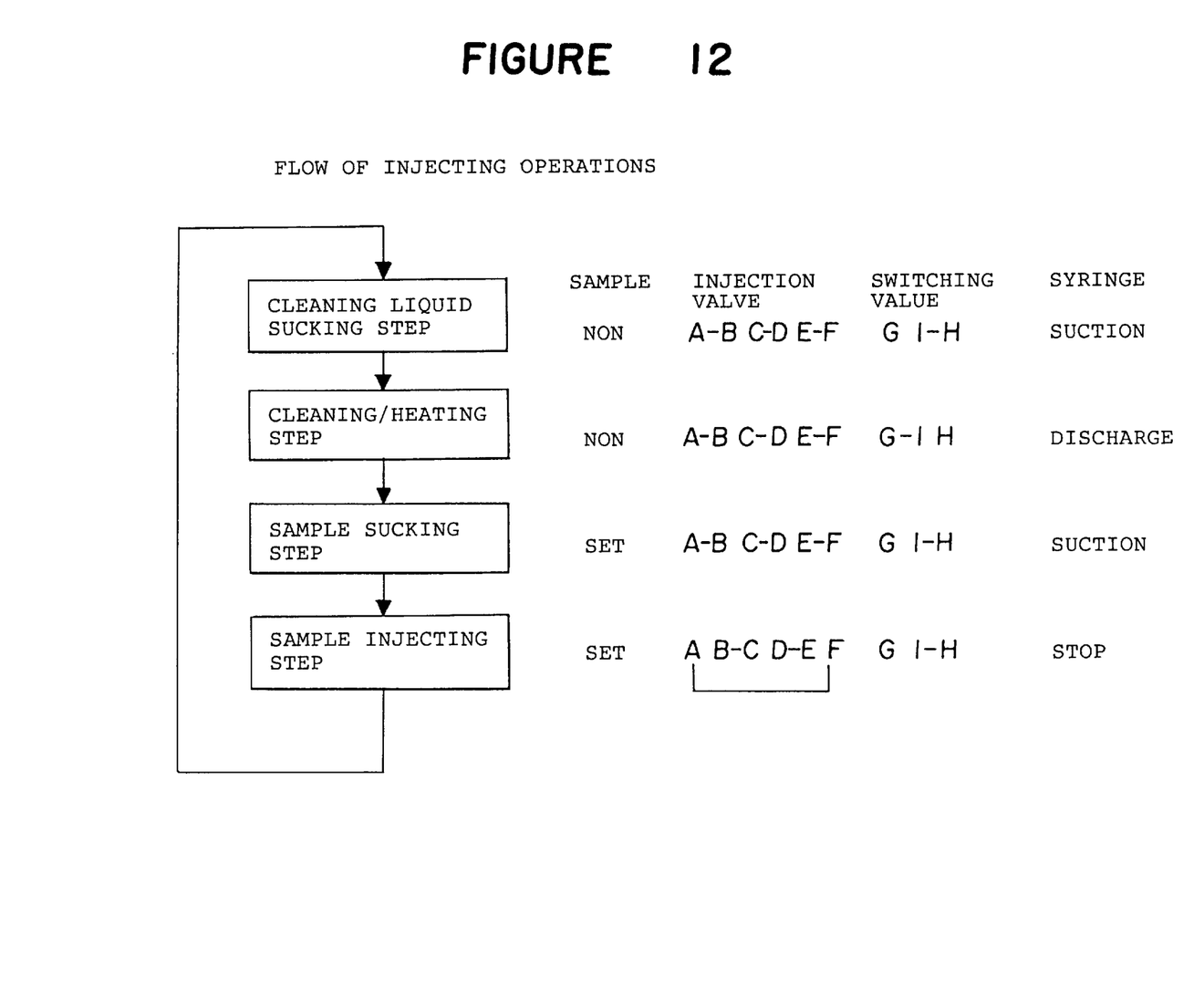
FIG. 12 is a diagram for explaining an example of a sample injecting method according to the present invention.

Sample injecting operations by the sample injecting apparatus shown in FIG. 10 comprises four steps: a cleaning liquid sucking step, a cleaning/heating step, a sample sucking step and a sample injecting step. FIG. 12 shows a flow chart of these steps, and FIG. 13 shows actual operations of the sample injecting apparatus.

Figure 13A:
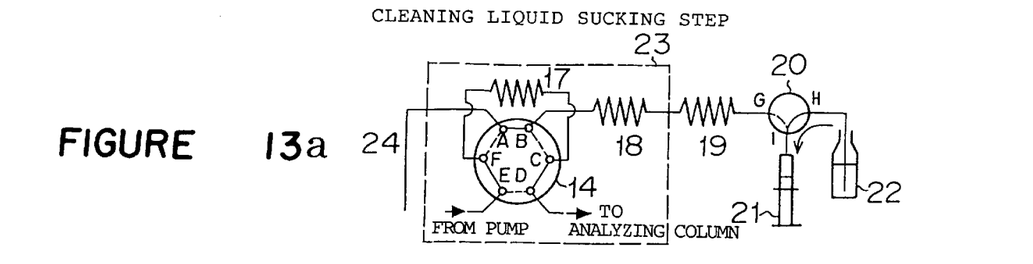
FIGS. 13a, 13b, 13c, and 13d are a diagram for explaining another embodiment of the sample injecting method according to the present invention.

The cleaning liquid sucking step is conducted by using a flow path shown in FIG. 13a. In this step, the sample injecting means (6-port-switching valve) 14 is in a state that ports A–B, C–D and E–F are respectively communicated, and the switching valve 20 is in a state that ports I–H are communicated. In such states, the metering means (syringe) 21 is operated (by pulling the plunger) to inject the cleaning liquid kept at the room temperature into the sample injecting means 14.

Figure 13B:
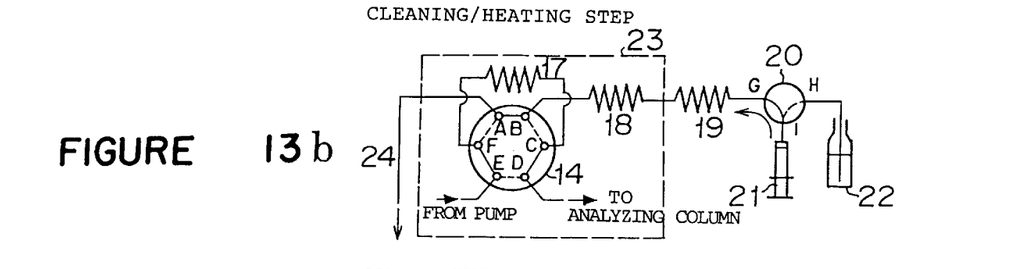

In the cleaning/heating step, a flow path shown in FIG. 13b is used. In this step, the sample injecting means (6-port-switching valve) is in a state that ports A–B, C–D and E–F are respectively communicated, and the switching valve 20 is in a state that ports I–G are communicated. In these states, the metering means (syringe) 21 is operated by pushing the plunger, whereby the cleaning liquid 22 in the sample injecting means is discharged through the sampling needle 24 via the second heat exchanger (cooling loop) 19, the first heat exchanger (preheating loop) 18 and the sample injecting means 14. In this step, the cleaning liquid 22 is heated to the same temperature as in the analyzing column while it is passed through the first heat exchanger (preheating loop) 18 in the oven 23 which is controlled to have the same temperature condition as the analyzing column. Thus, the cleaning liquid is heated finally to the same temperature as the analyzing column, namely a temperature capable of dissolving the sample, and then, the cleaning liquid is discharged through the sampling needle 24. The sampling needle 24 is kept under a room temperature condition and the cleaning liquid of high temperature can be passed therethrough. Even in a case of conducting the analyzing repeatedly, the needle 24 can be washed off without a danger that the sample in the last sample sucking operation is deposited on the needle 24.

Figure 13C:
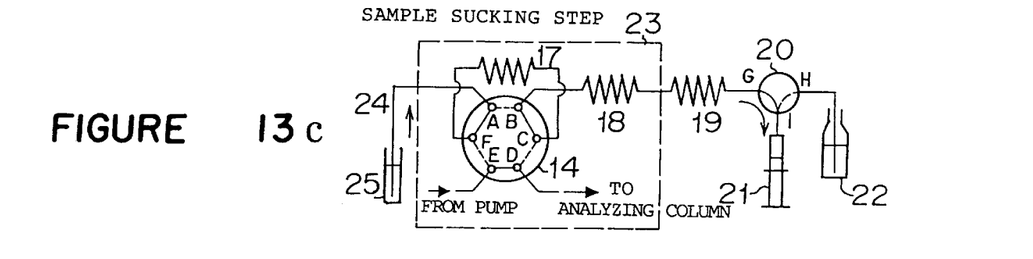

The sample sucking step is conducted by using a flow path shown in FIG. 13c. In this step, the sample injecting means (6-port-switching valve) 14 is in a state that ports A–B, C–D and E–F are respectively communicated, and the switching valve 20 is in a state that ports I–G are communicated. In these states, the sample 25 dissolved at a high temperature is placed below the sampling needle 24, and then, the needle 24 is descended into the sample. The metering means (syringe) 21 is operated by pulling the plunger so that the sampling loop 17 is filled with the sample 25. In this case, the cleaning liquid remaining in the sampling loop 17 and the first heat exchanger (preheating loop) 18 is passed through the second heat exchanger (cooling loop) 19 to be returned to the metering means (syringe) 21. Since the cleaning liquid in the sampling loop 17 and the first heat exchanger (preheating loop) 18 is under a high temperature condition by means of the oven 23, it is kept at substantially the same temperature as the analyzing column. Then, the temperature of the cleaning liquid is decreased during being passed through the second heat exchanger (cooling loop) 19 before it is returned to the metering means (syringe) 21.

Figure 13D:
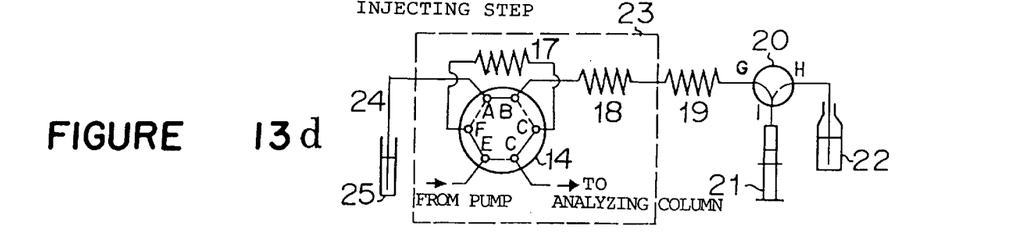

The sample injecting step is conducted by using a flow path shown in FIG. 13d. In this step, the sample injection means (6-port-switching valve) 14 is in a state that ports B–C, D–E and F–A are respectively communicated, and the sample introduced into the sampling loop 17 is supplied to the analyzing column in which separation and detection are carried out.

Thus, use of the sample injecting apparatus having the structure shown in FIG. 10 makes it unnecessary to place the sampling needle and the metering means having a movable mechanical parts under a high temperature condition even in HPLC for analyzing the sample under a high temperature condition. Further, since it is unnecessary to place the cleaning liquid under a high temperature condition, the evaporation of the cleaning liquid and the leakage of it outside of the apparatus can be prevented. Accordingly, when the sample injecting apparatus is combined with the structure according to the first to third aspects of the present invention in which the precolumn and the analyzing column are connected through the switching valve, double effects of easiness of regenerating the precolumn and being applicable suitably to high temperature HPLC can be achieved.

EXAMPLE 1

Analysis of standard polystyrene was conducted by GPC as shown in FIG. 7. The standard polystyrene was used as a sample; the amount of the sample injected was 300 $\mu$l and the amount of liquid supplied from the pump was 1 ml/min. The precolumn used was a commercially available column (tradename: TSKgel GMH manufactured by TOSOH CORPORATION, 7.8 mm (inner diameter)×3 cm (length)). The analyzing column used was three commercially available analyzing columns connected in series (tradename: TSKgel GMH manufactured by TOSOH CORPORATION, 7.8 mm (inner diameter)×30 cm (length)). Ovens 7 and 8 for housing these columns were controlled to be at 50° C. These columns were previously used for analyzing standard polystyrene for a long term prior to measuring the pressure of the pump.

Figure 8:
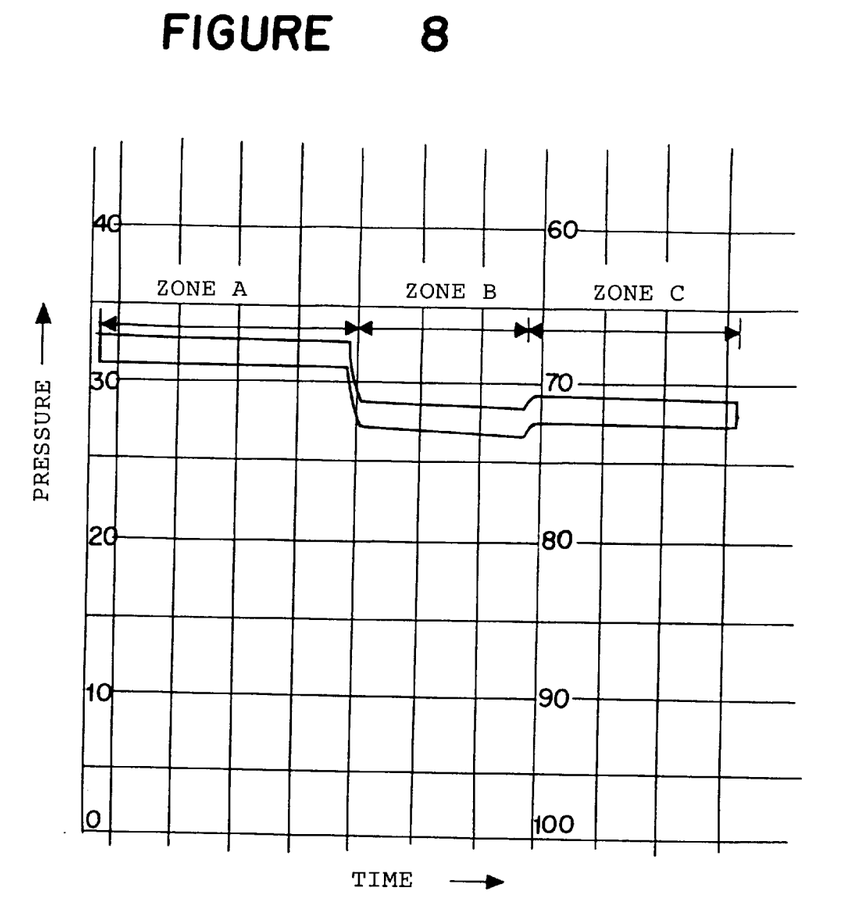
FIG. 8 is a graph showing a result of the example wherein the ordinate represents liquid supply pump pressure and the abscissa represents time.

FIG. 8 is a diagram showing a change of pressure in the pump in switching operations of the valve. In FIG. 8, a zone A shows a pressure change in an analyzing operation; a zone B shows a pressure change when the flow path for analyzing operation is switched to the flow path for regeneration; and a zone C shows a pressure change when the flow path for regeneration is again switched to the flow path for analyzing. As understood from the Figure, there is found a substantial reduction of pressure when the flow path for analyzing is switched to the flow path for regeneration. Even when the flow path for regeneration is switched to the flow path for analyzing, there is no possibility of pressure increase to the original pressure since scraps and so on deposited at the end of the precolumn has already been discharged out of the system.

EXAMPLE 2

The sample injecting apparatus shown in FIG. 10 was applied to the high temperature GPC. The conditions for the high temperature GPC were as follows. ODCB was used as the solvent (cleaning liquid) 22; polyethylene was used as the sample 25 to be analyzed; and the capacity of the metering means (syringe pump) 21 was 1 ml. The sample was dissolved in the solvent which was heated to 150° C., and temperature in the ovens 27 and 28 was set to 150° C. An amount of the sample to be analyzed was 300 $\mu$l, and accordingly, the capacity of the sampling loop 17 was 300 $\mu$l. The capacities of the first heat exchanger (preheating loop) 18 and the second heat exchanger (cooling loop) 19 were respectively 2 ml so as to obtain sufficient heat exchange.

An amount of the liquid supplied from the pump (not shown) was 1 ml/min. A serial connection of commercially available analyzed columns (three columns connected in series, tradename: TSKgel GMH manufactured by TOSOH CORPORATION, each 7.8 mm (inner diameter)×30 cm (length)), the three columns being housed in an oven which was temperature-controlled to be about 150° C. and a commercially available refractometer is connected to a port D. No precolumn was connected.

First, the sample injecting means 14 was brought into a state that ports A–B, C–D and E–F were communicated, and the switching valve 20 was brought into a state that ports I–H were communicated, and then, the cleaning liquid sucking step was conducted. Namely, the plunger of the syringe 21 was pulled to fill the 1 ml syringe with the cleaning liquid 22.

Then, the sample injecting means 14 was brought into a state that ports A–B, C–D and E–F were communicated and the switching valve 20 was brought into a state that ports I–G were communicated, and then, the cleaning/heating step was conducted. Namely, the plunger of the syringe 21 was pushed to discharge the cleaning liquid in an amount of 1 ml through the sampling needle 24 while the cleaning liquid was heated during which the analyzing columns is washed and the sampling needle is heated.

Then, the sample injecting means 14 was brought into a state that ports A–B, C–D and E–F were communicated, and the switching valve was brought to a state that ports I–G were communicated, and the sample sucking step was conducted. Namely, the dissolved sample 25 was placed below the sampling needle 24, and the needle 24 was descended into the sample. Then, the plunger of the syringe 21 was pulled to suck the sample by an amount of 0.5 ml to fill the sample in the sampling loop 17.

Then, the sample injecting means 14 was brought into a state that ports B–C, D–E and F–A were communicated, and an amount of 300 μl of the sample in the sampling loop 17 was introduced into the analyzing column (not shown). After the sample was injected, the cleaning liquid sucking step and cleaning/heating step were conducted to wash off the sample remaining in the sampling needle.

Figure 14:
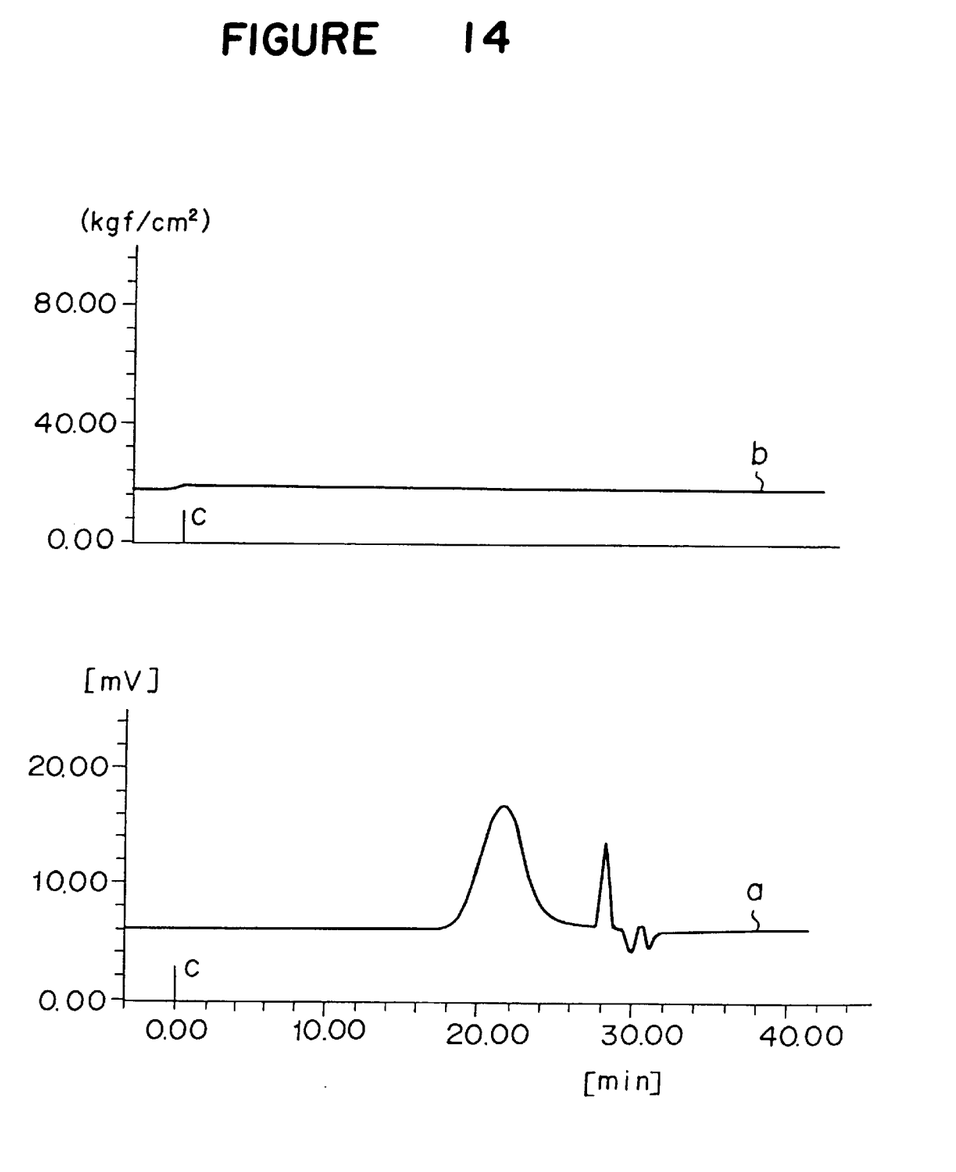
FIG. 14 shows chromatograms which show results of examples of sample injection by using the apparatus and the method of the present invention.

FIG. 14 shows a result of the analysis wherein symbol a indicates a signal of the refractometer, symbol b indicates the pressure of the pump, and the symbol c indicates the time of starting injection of the sample. Deposition of the injected sample in the flow path frequently cause clogging of the flow path to result a pressure increase and a large disturbance of signal in the refractometer. However, in the apparatus shown in FIG. 10, there was no found an increase of pressure in the pump and a disturbance of signal in the detector whereby a preferred chromatogram was obtainable.

According to an aspect of the present invention, the regeneration of the precolumn is possible without detaching the precolumn. Accordingly, since the work for detaching the precolumn is unnecessary, the regenerating treatment can quickly, easily be conducted with the result that interruption of analysis can be short. Further, the quick, easy regeneration of the precolumn can reduce the occurrence of a pressure increase of pump due to the deposition of scraps on the precolumn.

In particular, in HPLC in GPC, the washing-off and regeneration of the precolumn can be conducted by using only the solvent for analyzing without using the solvent for regeneration. Further, use of a single pump is enough to supply the liquid in the regeneration. In addition, the same kind of solvent can be introduced into the first column and the second column to regenerate the precolumn. Accordingly, there is no problem that it takes a longer time to equilibrate the analyzing column after the regeneration. Even in HPLC in a mode other than GPC, the same kind of solvent can be supplied to the first column and the second column irrespective of analyzing or regenerating.

Thus, since the regeneration of the precolumn can quickly, easily be done, service lives of the precolumn and the analyzing column can be prolonged. Even in a case of exchanging the precolumn, it is possible to finish the equilibration of the analyzing column in a shorter time whereby efficiency of analyzing can remarkably be improved.

In the sample injecting apparatus used in the liquid chromatograph apparatus according to the fourth and fifth aspects of the present invention, it is possible to place the metering means, the cleaning liquid and so on under a different temperature condition, normally, under a room temperature condition from that for the analyzing column, by placing only minimum necessary mechanical elements under the same temperature condition as the analyzing column. Accordingly, occurrence of a defective movement of the mechanical elements in the sample injecting apparatus can be minimized. Further, since an element (such as a sealing material) used in a portion in contact with the sample or the solvent and so on is disposed under a room temperature condition, a danger of decreasing its strength can be minimized. Further, since the cleaning liquid is disposed under a room temperature condition, evaporation of the cleaning liquid can be prevented so that leakage of the cleaning liquid out of the system can be minimized. In particular, the sample injecting apparatus is suitable as an apparatus for injecting the sample into the analyzing column under a high temperature condition of exceeding 100° C.

Accordingly, the liquid chromatograph apparatus provided with the sample injecting apparatus according to the fourth and fifth aspects can provide quick, easy regeneration of the precolumn and minimizes occurrence of a defective operation of the mechanical elements in the sample injecting apparatus. In particular, the liquid chromatograph apparatus is suitable for high temperature HPLC.

I claim:

1. In a liquid chromatograph apparatus comprising a first column and a second column which are connected through a switching means, the liquid chromatograph apparatus being characterized in that said switching means comprises a valve body capable of switching between at least two movable positions wherein a flow path for a solvent directing from the first column to the second column is formed in one of the two movable positions; a flow path for the solvent directing from the second column to the first column is formed in the other of the two movable positions, and the flow paths formed in the two movable positions are such that flowing directions of the solvent in the first column are opposite and flowing directions of the solvent in the second column are the same.

2. The liquid chromatograph apparatus according to claim 1, wherein said switching means is a two-position-switching valve having at least 8 ports.

3. The liquid chromatograph apparatus according to claim 1, wherein said switching means is formed by combining two or more two-position-switching valves each having at least 6 ports.

4. The liquid chromatograph apparatus according to claim 1, which further comprises a sample injecting apparatus including a sample injecting means provided with a sampling needle and a sampling loop, a first heat exchanger, a second heat exchanger, a metering means and a cleaning liquid containing vessel, wherein a portion of the sample injecting means excluding at least the sampling needle and the first heat exchanger are kept under the same temperature condition as the columns; at least the second heat exchanger, the metering means and the cleaning liquid containing vessel are kept at a temperature different from the temperature in said portion and the first heat exchanger; and the sample injecting means, the first heat exchanger, the second heat exchanger, the metering means and the cleaning liquid containing vessel are connected in series.

5. The liquid chromatograph apparatus according to claim 4, wherein said sample injecting means is a two-position-switching valve having 6 ports.

\* \* \* \* \*